(12) United States Patent
Rothenfusser

(10) Patent No.: US 10,217,560 B2
(45) Date of Patent: Feb. 26, 2019

(54) INDUCTOR

(71) Applicant: Siemens Aktiengesellschaft, Munich (DE)

(72) Inventor: Max Rothenfusser, Munich (DE)

(73) Assignee: SIEMENS AKTIENGESELLSCHAFT, Munich (DE)

(*) Notice: Subject to any disclaimer, the term of this patent is extended or adjusted under 35 U.S.C. 154(b) by 37 days.

(21) Appl. No.: 15/110,877

(22) PCT Filed: Jan. 21, 2015

(86) PCT No.: PCT/EP2015/051091
§ 371 (c)(1),
(2) Date: Jul. 11, 2016

(87) PCT Pub. No.: WO2015/117820
PCT Pub. Date: Aug. 13, 2015

(65) Prior Publication Data
US 2016/0351326 A1    Dec. 1, 2016

(30) Foreign Application Priority Data

Feb. 6, 2014    (DE) .................. 10 2014 202 128

(51) Int. Cl.
| | | |
|---|---|---|
| *H01F 5/00* | (2006.01) | |
| *H01F 27/29* | (2006.01) | |
| *H05B 6/36* | (2006.01) | |
| *H01F 38/30* | (2006.01) | |
| *H01F 27/28* | (2006.01) | |
| *H01F 37/00* | (2006.01) | |

(Continued)

(52) U.S. Cl.
CPC .............. *H01F 27/29* (2013.01); *H01F 5/00* (2013.01); *H01F 27/2823* (2013.01); *H01F 37/005* (2013.01); *H01F 38/00* (2013.01); *H01F 38/30* (2013.01); *H05B 6/36* (2013.01); *G01N 25/72* (2013.01)

(58) Field of Classification Search
CPC .................. H01F 5/00; H01F 27/00–27/36
USPC ............................................ 336/65, 200, 232
See application file for complete search history.

(56) References Cited

U.S. PATENT DOCUMENTS

| | | | | |
|---|---|---|---|---|
| 3,449,664 A | * | 6/1969 | Smith ............... | G01N 27/9046 324/235 |
| 6,677,561 B1 | | 1/2004 | Koppinen et al. ........... | 219/645 |

(Continued)

FOREIGN PATENT DOCUMENTS

| | | | | |
|---|---|---|---|---|
| CN | 1706225 A | 12/2005 | ............... | C21D 9/00 |
| CN | 1764989 A | 4/2006 | ............... | C21D 1/10 |

(Continued)

OTHER PUBLICATIONS

Chinese Office Action, Application No. 201580002831.5, 5 pages, dated Apr. 5, 2017.

(Continued)

*Primary Examiner* — Tuyen Nguyen
(74) *Attorney, Agent, or Firm* — Slayden Grubert Beard PLLC

(57) ABSTRACT

An inductor for induction thermography may be designed, in at least one section, as a rectangularly wound conductor that includes a closed conductor loop which, except for a conductor forming the conductor loop, is free from electrical components.

8 Claims, 4 Drawing Sheets

(51) Int. Cl.
*H01F 38/00* (2006.01)
*G01N 25/72* (2006.01)

(56) References Cited

U.S. PATENT DOCUMENTS

| | | | |
|---|---|---|---|
| 6,859,125 B2 | 2/2005 | Rudnev et al. | 336/55 |
| 7,283,345 B2* | 10/2007 | Liu | H03K 17/6877 361/118 |
| 7,485,882 B2 | 2/2009 | Zombo et al. | 250/504 R |
| 7,642,891 B2 | 1/2010 | Einzinger et al. | 336/226 |
| 2005/0275629 A1* | 12/2005 | Chin | G06F 3/03543 345/163 |
| 2015/0057653 A1* | 2/2015 | Sugiyama | A61B 17/3421 606/34 |
| 2015/0134273 A1 | 5/2015 | Bienkowski et al. | 702/38 |

FOREIGN PATENT DOCUMENTS

| | | | | |
|---|---|---|---|---|
| DE | 102012008531 A1 | 10/2013 | | G01N 25/72 |
| DE | 102012212434 A1 | 1/2014 | | G01N 25/72 |
| EP | 2386850 A2 | 11/2011 | | G01N 25/72 |
| JP | 5329183 A | 3/1978 | | C21D 1/42 |
| JP | 57141542 A | 9/1982 | | G01N 25/72 |
| JP | 5930052 A | 2/1984 | | G01N 21/88 |
| JP | 61132848 A | 6/1986 | | G01B 11/30 |
| JP | 61230053 A | 10/1986 | | G01N 21/89 |
| JP | 0413956 A | 1/1992 | | B21C 51/00 |
| JP | 0471159 A | 3/1992 | | H01J 61/32 |
| JP | 04178552 A | 6/1992 | | G01N 25/72 |
| JP | 07174722 A | 7/1995 | | G01J 5/10 |
| JP | 2005534184 A | 11/2005 | | H01F 17/00 |
| JP | 2009111959 A | 5/2009 | | H01Q 5/10 |
| WO | 98/19318 A1 | 5/1998 | | H01F 17/04 |
| WO | 2009/080318 A1 | 7/2009 | | G01N 21/89 |
| WO | 2014/012716 A1 | 1/2014 | | G01D 7/00 |
| WO | 2015/117820 A1 | 8/2015 | | G01N 25/72 |

OTHER PUBLICATIONS

German Office Action, Application No. 102014202128.6, 7 pages, dated Jan. 30, 2015.
International Search Report and Written Opinion, Application No. PCT/EP2015/051091, 11 pages, dated May 11, 2015.
Japanese Office Action, Application No. 2016550564, 4 pages, dated Jul. 3, 2017.
Chinese Office Action, Application No. 201580002831.5, 6 pages, dated Dec. 29, 2017.

* cited by examiner

INDUCTOR

CROSS-REFERENCE TO RELATED APPLICATIONS

This application is a U.S. National Stage Application of International Application No. PCT/EP2015/051091 filed Jan. 21, 2015, which designates the United States of America, and claims priority to DE Application No. 10 2014 202 128.6 filed Feb. 6, 2014, the contents of which are hereby incorporated by reference in their entirety.

TECHNICAL FIELD

The invention relates to an inductor for induction thermography.

BACKGROUND

One method for detecting defects of an object, in particular of a component, is induction thermography. In induction thermography, by means of an inductor which is guided over the object to be tested (test object), an induction current is excited in the test object. A defect in the test object, particularly in the component, leads to a local disruption of the induction current and consequently to a local change in the heating of the test object by ohmic losses. The change in the local heating is in turn recorded by means of an infrared camera, so that detection of the defects is possible by evaluation of the infrared image that has been recorded by means of the infrared camera.

According to the prior art, the inductors for the testing are arranged at a small distance above the test object. In this case, the maximum amplitude of the induction current excited in the test object lies directly below the conductors of the inductor. This gives rise to the disadvantage that precisely this region that is of interest for the detection of defects is covered by the conductors of the inductor, so that it is scarcely possible to record the region by an infrared camera arranged above the inductor.

Another disadvantage of known inductors is the strong dependency of the induction current at a position of the test object on the distance of the position from the conductor of the inductor. Particularly around the regions with the maximum amplitude of the induction current, this gives rise to an inhomogeneous distribution of the amplitude which makes reliable detection of defects and their size more difficult.

SUMMARY

One embodiment provides an inductor for induction thermography, which is configured at least in a subregion as a rectangularly wound conductor, wherein the conductor comprises a closed conductor loop which, apart from a conductor which forms the conductor loop, is free of electrical components.

In one embodiment, the conductor loop comprises two elementary conductors arranged at a distance from one another, the two elementary conductors having a constant distance from one another.

In one embodiment, the elementary conductors essentially fully form one side of the rectangle formed by the conductor.

In one embodiment, the one side is configured as a longitudinal side of a rectangularly wound conductor.

In one embodiment, the individual elementary conductors of the conductor loop are wound in elliptical segment fashion.

In one embodiment, the conductor loop is rectangularly wound.

In one embodiment, the inductor has two electrical terminals.

Another embodiment provides a method for using an inductor for induction thermography, wherein an alternating current flows through a conductor which is wound rectangularly at least in a subregion, the alternating current being divided along the conductor by a conductor loop into two elementary alternating currents flowing in parallel.

In one embodiment, a frequency of the alternating current lies in the frequency range of from 100 kHz to 500 kHz.

In one embodiment, a current strength of the alternating current is at least 1000 A.

BRIEF DESCRIPTION OF THE DRAWINGS

Example aspects and embodiments of the invention are described below with reference to the drawings, in which.

DETAILED DESCRIPTION

Figure 1:
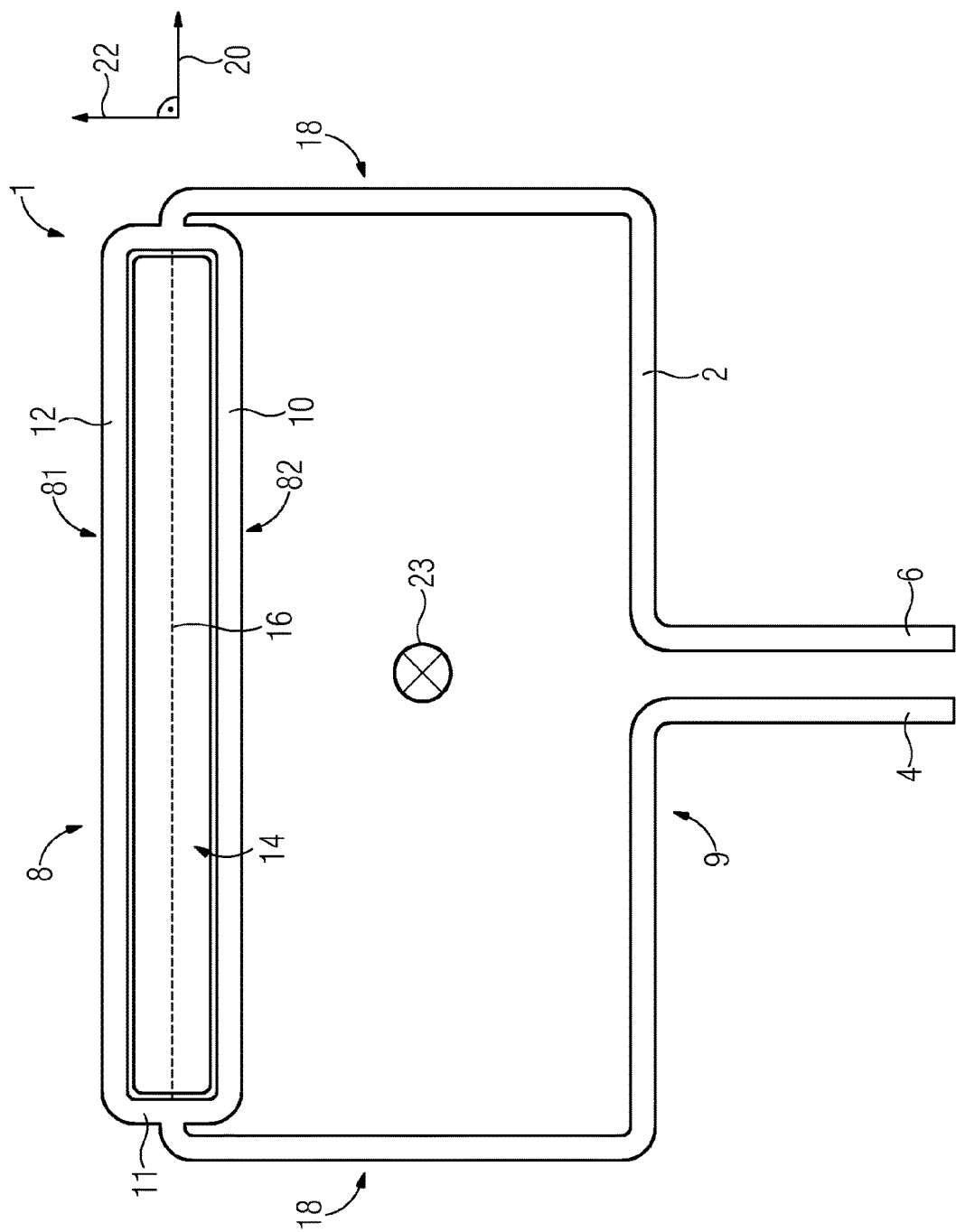
FIG. 1 shows a rectangularly wound inductor having a rectangular conductor loop, the conductor loop comprising two parallel-separated elementary conductors.

Embodiments of the present invention provide an inductor for induction thermography, which may avoid the aforementioned disadvantages of the prior art.

The disclosed inductor for induction thermography is configured at least in a subregion as a rectangularly wound conductor, the conductor comprising at least one closed conductor loop which, apart from a conductor which forms the conductor loop, is free of electrical components.

Because of the at least one conductor loop of the conductor, or of the inductor, a viewing window is formed which is advantageous for the thermographic recording of an image of the heat distribution of a test object. For example, the recording may be carried out by an infrared camera which uses the viewing window for the recording. A region with the maximum amplitude of the induction current is therefore recorded. Covering of the region by the conductor of the inductor is therefore avoided. A multiplicity of conductor loops may be provided. Besides the electrical conductor which forms the conductor loop, and the electrical properties of this conductor, in some embodiments the conductor loop of the inductor comprises no other electrical components, for example additional resistances, inductances and/or capacitances.

Another particular advantage of the closed inner conductor loop is that the amplitude of the induction current is homogenized in its maximum region. Inside the conductor loop, and therefore in the region of the viewing window, this gives rise to an essentially homogeneous spatial distribution of the amplitude of the induction current, and therefore of the induction current as a whole (in general, the induction current has an amplitude and a phase). In this case, the viewing window substantially corresponds to the region of the maximum amplitude of the induction current. Because of the spatial homogenization of the induction current, the detectability of defects of the test object is improved and furthermore remains almost constant in the region of the viewing window. Another advantage of the homogenization of the induction current is that a heat flux perpendicularly to the conductor of the inductor is reduced, so that thermal stagnations at edges, corners or interfaces of the test object are reduced. Furthermore, the region of the maximum amplitude of the induction current is increased by the conductor loop. The recording region, usable for the evaluation, of an infrared camera is thereby advantageously increased.

In the disclosed method for operating an inductor for induction thermography, an alternating current flows through a conductor which is wound rectangularly at least in a subregion, the alternating current being divided along the conductor by means of a conductor loop into two elementary alternating currents flowing in parallel.

Advantageously, the elementary alternating currents in the conductor loop are in-phase. This gives rise, in particular on a lower side of the inductor, facing toward the test object, to constructive superposition of the induction currents generated by the elementary alternating currents. An alternative way of considering this is to look at the magnetic fields. The magnetic fields generated by the elementary alternating currents are in-phase, particularly on the lower side facing toward the test object, so that constructive superposition (reinforcement) of the magnetic fields takes place, which likewise leads to the above-described superposition of the induction currents.

According to one embodiment, the conductor loop comprises at least two elementary conductors arranged at a distance from one another, the two elementary conductors having a constant distance from one another.

Because of the constant separation of the two elementary conductors, the induction current is advantageously approximately homogeneous inside the viewing window, so that the detectability and comparability of defects of the test object is improved.

According to one embodiment, the conductor loop comprises two elementary conductors separated with a constant distance, which essentially fully form one side of the rectangle formed by the conductor.

This may advantageously provide an increased viewing window, so that the recording region of the infrared camera is widened.

The distance between the two uniformly separated elementary conductors is adapted to the task. A small distance leads to greater homogenization than a large distance. A large distance increases the viewing window and therefore the recording region. In this case, a small distance is intended to mean a distance which is less than a width typical of the spatial variation of the amplitude of the elementary induction currents, in which case the spatial variation of the amplitudes of the elementary induction currents perpendicularly to the elementary conductors is to be used for the comparison. The elementary induction currents are the induction currents which each individual elementary conductor excites in the test object.

According to another embodiment, the one side is configured as a longitudinal side of the rectangularly wound conductor.

The viewing window may be increased further in this way, so that a large region of the test object is recorded by the infrared camera.

In one embodiment, the individual elementary conductors of the conductor loop are wound in elliptical segment fashion.

Firstly, distinction may be made between two types of elementary conductors wound, or bent, in elliptical segment fashion. According to a first type, the elementary conductors are wound in elliptical segment fashion in a plane in which the rectangular subregion of the conductor lies. According to a second type, the elementary conductors are wound in elliptical segment fashion in a plane perpendicular to the plane in which the rectangular subregion of the conductor lies.

In the type mentioned first, as seen from an observation direction, the elementary conductors form an elliptical arc, in particular an elliptical semi-arc, the arc lying essentially in a plane with the rectangular subregion of the conductor. In other words, the elementary conductors continue the rectangular subregion of the conductor as a protrusion in elliptical arc fashion of the one side of the conductor. This gives rise to a viewing window which is advantageous in particular for a bent subregion of a test object and/or bent test objects, the surface to be tested of which is, however, essentially planar. For example, an inductor of the first type mentioned is advantageous for testing a component of a combustion chamber of a gas turbine.

According to the type mentioned second, the conductor loop appears rectangular as seen from the observation direction. Because of the elliptical segment-like elementary conductors, there is now a non-twisted viewing window bent toward the test object or away from the test object. Because of the bending of the viewing window and the elliptical segment-like profile of the elementary conductors, which corresponds to this bending, an inductor is made possible for test objects whose surface to be tested is curved essentially only in one direction. The direction of the curvature of the surface corresponds to the bending of the viewing window, so that the bending, or the flat curvature of the viewing window replicates the curvature of the surface. The elementary conductors of the conductor loop therefore have an almost constant distance from the test object, so that the effect of the curvature of the surface to be tested on the amplitude of the induction current is compensated for by a curvature of the viewing window which replicates this curvature. An inductor having a viewing window curved in the manner described is advantageous in particular for testing turbine blades.

According to one embodiment, the conductor loop is rectangularly wound.

The conductor loop, as seen from the observation direction of the infrared camera, in this case has a rectangular shape. The rectangular shape of the conductor loop allows an expedient rectangular viewing window. An additionally flat, or planar, rectangular viewing window is preferred for test objects whose surface is essentially planar. In particular, a rectangular conductor loop which lies in a plane with the rectangular subregion of the conductor is advantageous here. For test objects whose surface facing toward the inductor is curved, a so to speak curved conductor loop is preferred. Despite the shape or curvature of the conductor loop, wound toward and/or away from the curved surface of the test object, the conductor loop has a rectangular shape as seen from the observation direction of the infrared camera.

According to one embodiment, the inductor comprises at least two electrical terminals.

In this way, the inductor can be connected to an external source for current and/or voltage supply. Advantageously, the electrical terminals of the one side of the inductor lie opposite and extend perpendicularly to the elementary conductors of the one side. Overall, the inductor is thus configured as a flat rectangularly wound conductor, the one side of the conductor being doubled by two parallel-separated elementary conductors.

According to one embodiment, a frequency of the alternating current lies in the frequency range of from 100 kHz to 500 kHz.

This leads according to the skin effect to an advantageous penetration depth of the induction current into the test object. For example, the penetration depths (skin depths) typically lie in the range of from 0.05 mm (ferromagnetic steel) to 2 mm (stainless steel).

According to another embodiment, a current strength of the alternating current is at least 1000 A.

Because of the high current strength of the alternating current, of at least 1000 A, correspondingly strong magnetic fields, which in turn excite large induction currents in the test object are formed. In this way, the detection of defects of the test object by the infrared camera is advantageously facilitated and improved.

FIG. 1 shows an inductor 1, which is configured as a rectangularly wound conductor 2 and whose first longitudinal side 8 comprises a closed conductor loop 11. The conductor loop 11 is essentially configured as a rectangle having two parallel longitudinal sides 81, 82, the longitudinal sides 81, 82 being formed from two elementary conductors 10, 12 arranged with parallel separation and essentially fully forming the first longitudinal side 8 of the conductor 2. In this case, the elementary conductors 10, 12 extend almost fully along the first longitudinal side 8. The first longitudinal side 8 lies with parallel separation opposite a second longitudinal side 9, which comprises two electrical terminals 4, 6. The electrical terminals 4, 6 extend perpendicularly to the longitudinal sides 8, 9 and parallel to the width sides 18 of the conductor 2.

By the conductor loop 11, a viewing window 14 is formed inside the inductor, which is used to record the heat distribution of a test object by means of an infrared camera (not represented). The inductor 1 can therefore be formed figuratively from doubling of a conductor 16 of a simply rectangularly wound conductor. In other words, the conductor loop 11 is formed from a parallel circuit of the two elementary conductors 11, 12.

In general, the conductor loop 11 does not have an additional electrical resistance, an additional resistance being intended to mean any electrical resistance which goes beyond the electrical line resistance of the conductor loop 11.

The elementary conductors 10, 12 extend parallel to a direction 20 (x direction). The amplitude of the induction current along the direction 20 is therefore almost constant. In a direction 22 (y direction), perpendicular to the direction 20, the amplitude of the induction current is essentially constant over the region of the viewing window 14 because of the doubling of the conductor 2 into the two elementary conductors 10, 12.

Typically, the inductor 1 represented in FIG. 1 is guided over a test object (not shown in FIG. 1). In this case, a distance of less than 1 cm between the inductor 1 and the test object is provided. The test object lies below the inductor 1 in relation to a z direction, which is antiparallel to an observation direction 23 of the infrared camera, the inductor 1 being arranged between the test object and the infrared camera in the manner represented in FIG. 1. The heat distribution on the test object is then recorded through the viewing window 14 by means of the infrared camera.

Figure 2:
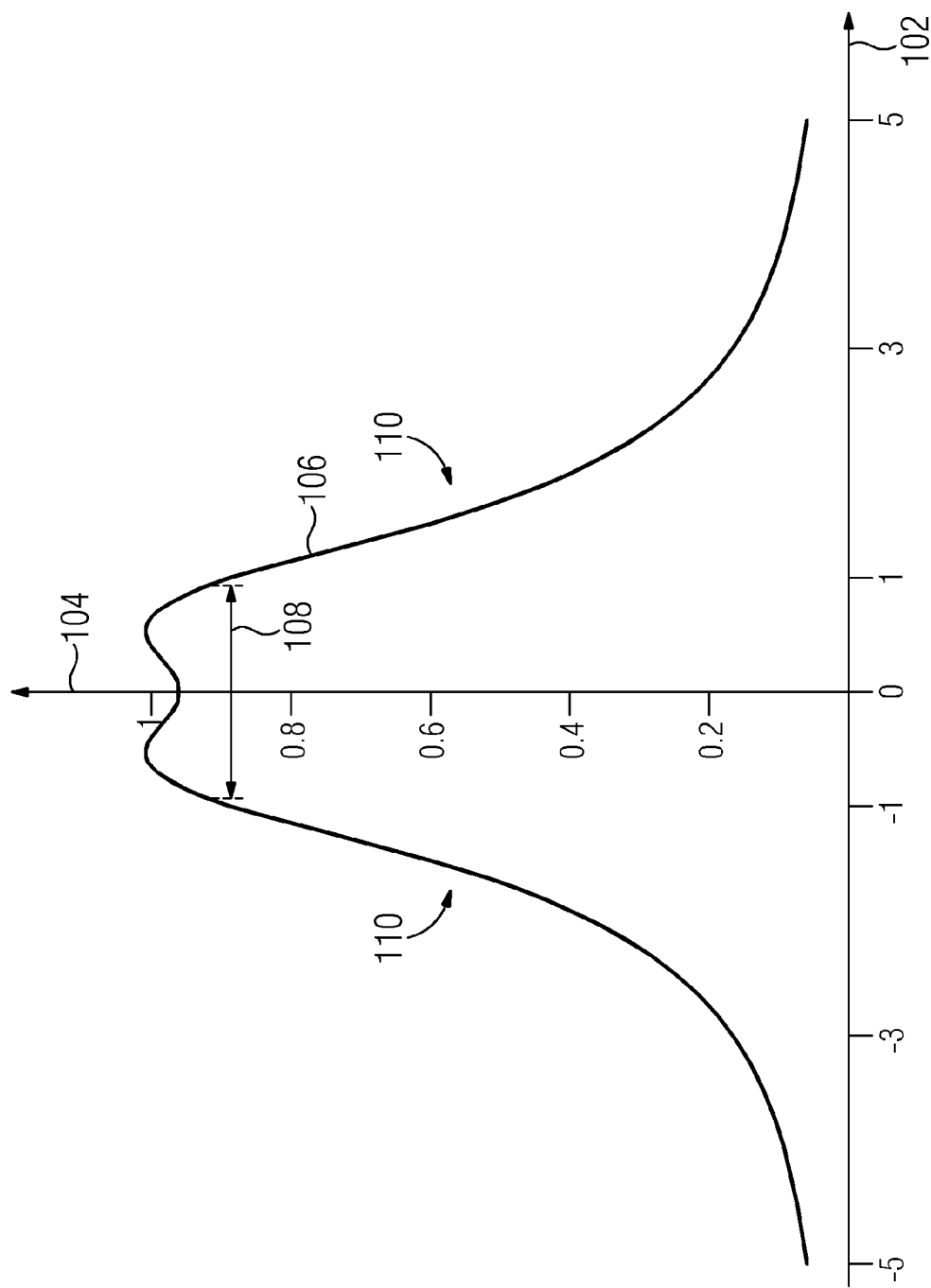
FIG. 2 illustrates a spatial variation of the amplitude of the induction current.

FIG. 2 shows the spatial variation of the amplitude 106 of the induction current along the direction 22. Here, the relative distance (with a sign) along the direction 22 is plotted on the abscissa 102, the zero value of the relative distance corresponding to the imaginary conductor 16. The elementary conductors 10, 12 have a distance which is equal in magnitude from the imaginary conductor 16, so that the imaginary conductor 16 lies centrally between the two elementary conductors 10, 12. The amplitude 106, normalized to its maximum, of the induction current is plotted on the ordinate 104.

The homogeneous region 108, which essentially corresponds to the width of the viewing window 14 along the direction 22, can be seen clearly. Although there is a small variation of the amplitude 106 of the induction current in the homogeneous region 108, this variation is nevertheless negligible in comparison with the steeply falling edges 110 of the amplitude 106. For a purely rectangularly wound inductor known from the prior art, the conductor of which follows in particular the imaginary conductor 16, the homogeneous region 18 would essentially be reduced to a point.

Figure 3:
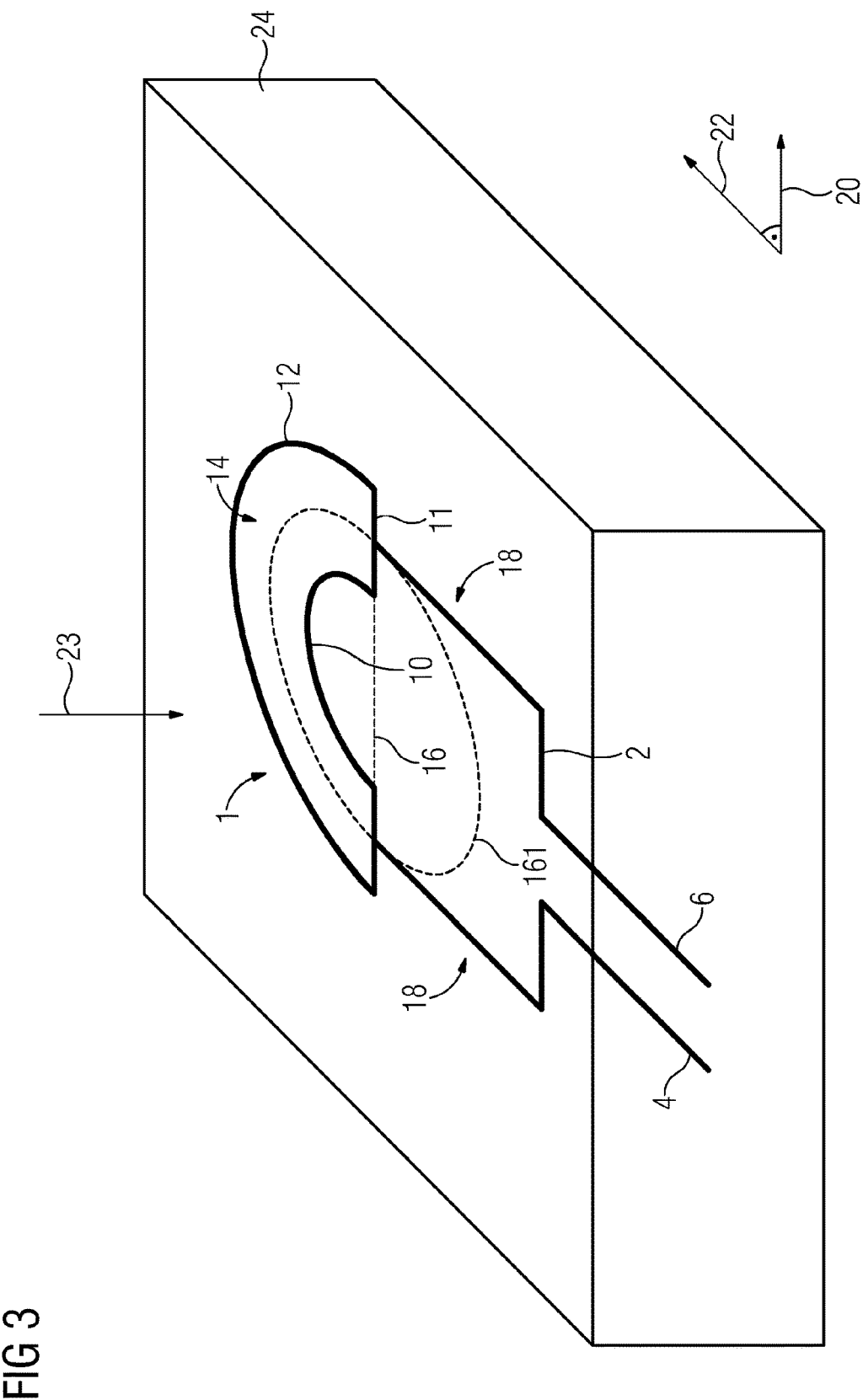
FIG. 3 shows a three-dimensional representation of a rectangularly wound inductor having a conductor loop, the elementary conductors of the conductor loop being wound in elliptical segment fashion.

FIG. 3 shows a three-dimensional representation of an inductor 1, the conductor loop 11 of which extends along an elliptical arc 161. In this case, the elementary conductors 10, 12 are wound in elliptical segment fashion and lie with a constant separation in a plane with the rectangular subregion of the conductor 2. The elementary conductors 10, 12 therefore form a protrusion in elliptical segment fashion of the conductor 2, or of the inductor 1, which lies in said plane. Again, the inductor 1 lies above the test object 24 in relation to the z direction, which is antiparallel to the observation direction 23 of the infrared camera, the inductor 1 being arranged between the test object 24 and the infrared camera (not shown) in the manner illustrated in FIG. 3.

By the elementary conductors 10, 12 arranged separated and wound in elliptical segment fashion, a bent elliptical viewing window 14 is formed, which is preferred in particular for a subregion, bent in elliptical segment fashion, of a test object and/or bent test objects. In general, the viewing window 14 may be adapted to any desired geometrical shape of a test object by arrangement of the elementary conductors 10, 12.

Figure 4:
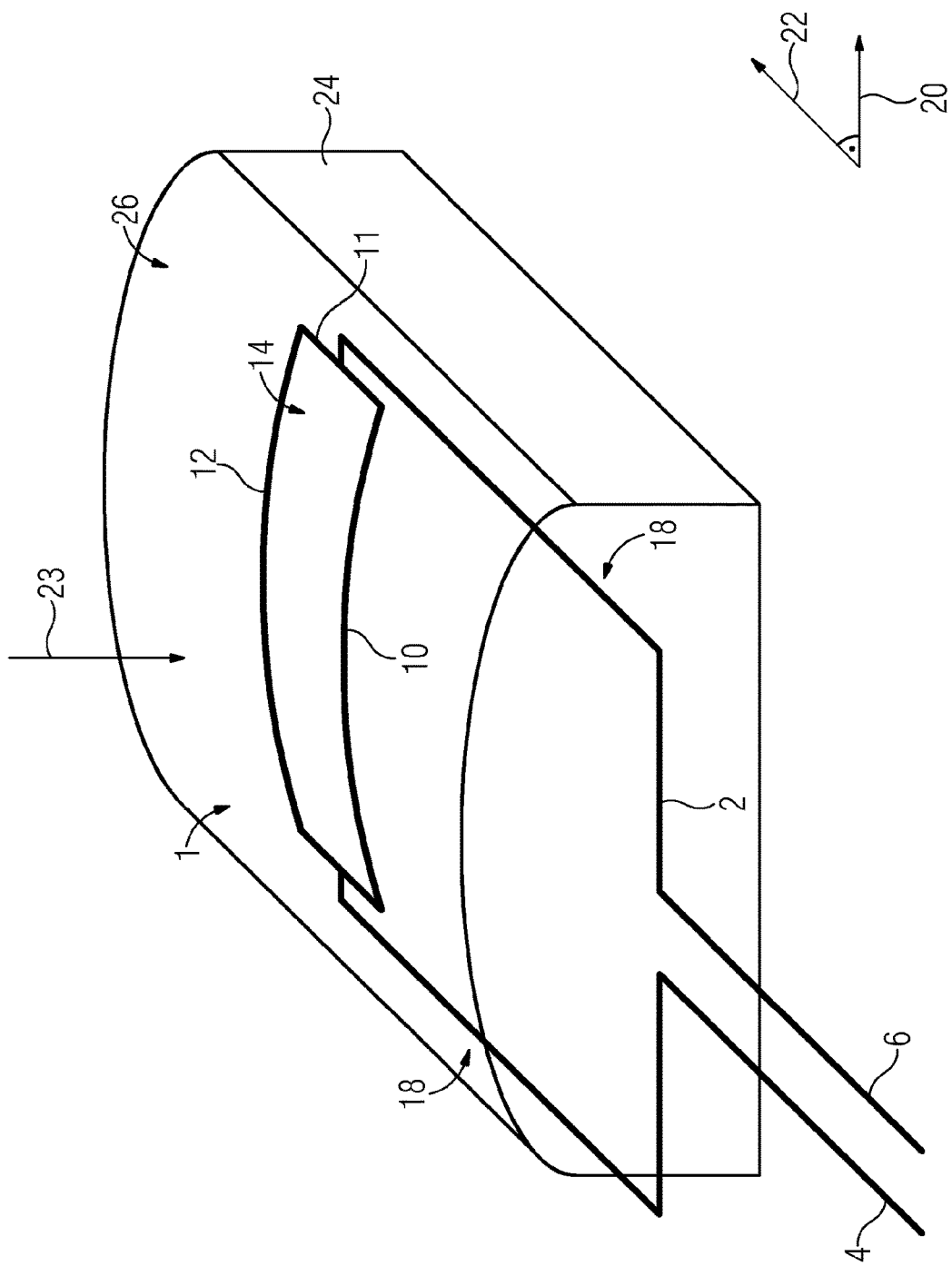
FIG. 4 shows a three-dimensional representation of a rectangular inductor having a rectangularly wound and flatly curved conductor loop.

FIG. 4 shows an inductor 1, the conductor loop 2 of which is configured rectangularly in a view parallel to the observation direction 23. Basically, therefore, the inductor 1 shown here resembles that represented in FIG. 1. The only difference is that viewing the window 14 has a shape curved toward the test object because of the elementary conductors 10, 12 wound in elliptical segment fashion.

In contrast to FIG. 3, the elementary conductors 10, 12 are wound in elliptical segment fashion not in the plane of the rectangularly wound conductor 2, but in a plane perpendicular to said plane. The viewing window 14 and the wound conductor loop 11 therefore illustratively resemble a non-rotated bent rectangle which is bent toward the test object 24. Because of the bending of the viewing window 14, the viewing window 14 is adapted to the curved surface 26 of the test object 24. The adaptation is to be understood as meaning that the distance of the elementary conductors 10, 12 from the curved surface 26 of the test object 24 is essentially constant.

What is claimed is:
1. An inductor for induction thermography comprising:
a rectangularly wound conductor with two short sides and two long sides;
wherein one of the two long sides comprises a closed conductor loop forming a rectangle with two longitudinal sides perpendicular to two width sides, all four sides free of electrical components except for a conductor that forms the closed conductor loop;

wherein two electrical terminals extend out from a first longitudinal side and away from a second longitudinal side, perpendicular to the two longitudinal sides and parallel to the two width sides along the one of the two long sides of the rectangularly wound conductor.

2. The inductor of claim 1, wherein the closed conductor loop comprises two elongated elementary conductors arranged in parallel and separated from each other.

3. The inductor of claim 2, wherein the elementary conductors form the second longitudinal side of the rectangle.

4. The inductor of claim 1, wherein individual elementary conductors of the closed conductor loop are wound in a shape of elliptical segments.

5. The inductor of claim 1, wherein the closed conductor loop is rectangularly wound.

6. A method for using an inductor for induction thermography, the method comprising:

flowing an alternating current along a conductor wound rectangularly at least in a subregion, and using a conductor loop in one long side of the rectangularly wound conductor to divide the alternating current flowing along the rectangularly wound conductor into two elementary alternating currents flowing in parallel, wherein the conductor loop comprises two elongated elementary conductors arranged in parallel and separated from each other and free from electrical components.

7. The method of claim 6, wherein a frequency of the alternating current lies in a frequency range of 100 kHz to 500 kHz.

8. The method of claim 6, wherein a current strength of the alternating current is at least 1000 A.

* * * * *